United States Patent [19]

Rüther

[11] Patent Number: 5,270,008
[45] Date of Patent: Dec. 14, 1993

[54] ANALYZING DEVICE

[75] Inventor: Horst Rüther, Graz, Austria

[73] Assignee: AVL Medical Instruments AG, Schaffhausen, Switzerland

[21] Appl. No.: 876,374

[22] Filed: Apr. 30, 1992

[30] Foreign Application Priority Data

Oct. 9, 1991 [AT] Austria ................. A2005/91
Apr. 6, 1992 [AT] Austria ................. A718/92

[51] Int. Cl.$^5$ ........................................ G01N 35/02
[52] U.S. Cl. ............................ 422/68.1; 73/864.01; 422/81; 422/82
[58] Field of Search ............. 422/68.1, 81, 82; 73/864.01

[56] References Cited

U.S. PATENT DOCUMENTS 5,032,362  7/1991  Marsoner et al. ............. 422/81

Primary Examiner—Jill A. Johnston
Attorney, Agent, or Firm—Watson, Cole, Grindle & Watson

[57] ABSTRACT

An analyzing device, in particular for examining body fluids, with a measuring module, at least one gas feed tube for a calibrating gas, a moistening device for the calibrating gas as well as a washing water tube connectable to the measuring channel of the measuring module, is simplified and improved in that the moistening device for the calibrating gas is integrated in the washing water conduit through a water inlet and a water outlet. The calibrating gas can be led over the water surface in the moistening device and moistened in this way.

6 Claims, 2 Drawing Sheets

ANALYZING DEVICE

BACKGROUND OF THE INVENTION

The invention relates to an analyzing device, in particular for examining body fluids, with a measuring module, at least one gas feed tube for a calibrating gas, a moistening device for the calibrating gas as well as a washing water conduit connectable to the measuring channel of the measuring module.

DESCRIPTION OF THE PRIOR ART

Such an analyzing device is known, for example, from EPA 0 297 082. In addition to an input device for the samples, the measuring channel of the measuring module of this analyzing device can be connected, inter alia, with several calibrating gases and a washing water conduit through a docking element. In intervals that are preset or determined by the user, a cleaning liquid such as water flows from the water reservoir of the device through the measuring module. To moisten the calibrating gases they are injected from below into a moistening device container filled with water and allowed to pass through the water in form of bubbles. The container of the moistening device comprises valve-controlled supply connections to the water reservoir and to a waste container through which the water in the moistening device is automatically renewed within the predetermined time intervals. The disadvantage of this known analyzing device is the relatively high amount of control and monitoring devices which, on the one hand, are necessary for the washing device and, on the other hand, for the moistening device.

It is the object of the present invention to realize a simple inexpensive analyzing device that requires the fewest possible control elements for the moistening and cleaning functions.

SUMMARY OF THE INVENTION

This object is achieved in accordance with the invention in that the moistening device for the calibrating gas is integrated in the washing water conduit through a water inlet and a water outlet. This measure simplifies the device considerably because separate tubes or valves for the moistening device are no longer required. During each washing process of the measuring module water is taken from the reservoir of the device. It reaches the measuring channel of the measuring module through the moistening device, whereupon simultaneously the water level in the moistening apparatus is renewed in regular intervals.

Gases are usually moistened in such a way that they pass through the water reservoir in form of bubbles, as is known, for example, in the above-mentioned EPA 0 297 082. A disadvantage of this known method occurs when several calibrating gases or gas mixtures are required. Either one has to accept a relatively large interval for the retonometrification of the water or a separate moistening device has to be provided for each gas mixture. Retonometrification pertains here to the measure of replacing a certain gas that is dissolved in water by another gas.

It is a further object of the invention to shorten the time span for making moistened gases available even if only one moistening device is used. This object is achieved in accordance with the invention in that the introduction of the calibrating gas into the moistening device is carried out at the water level as defined by the water outlet, whereby the calibrating gas passes over the water surface after its introduction. If the gas stream moves over the water surface, it is easily possible to achieve moistening degrees of $>90°$. At the same time, the time span required for making available various moistened gases can be reduced by a wide margin because the absolute amount of water can be kept very low. In addition, it is not necessary to carry out a complete retonometrification of the water, because, as opposed to the known method, the residual gases that are dissolved in the water only have a very small influence on the calibrating gas flowing over the water surface.

In a further embodiment of the invention it is provided that the water inlet and the water outlet of the moistening apparatus are arranged at the same level and that the introduction of the calibrating gas is carried out through the water inlet, which ensures a particularly simple arrangement of the moistening device.

To prevent the gas flowing from the moistening apparatus from entraining water droplets into the gas tube, the moistening apparatus comprises, in accordance with the invention, a gas-permeable and water vapour-permeable blocking device that is arranged above the water level and below an opening for discharging the moistened calibrating gas. Preferably, the blocking device may be a gas-permeable or water vapour-permeable membrane. Furthermore, the blocking device may also consist of a small plate with at least one small bore.

Finally, it is provided in accordance with the invention that the blocking device comprises a chamber for separating water drops, which chamber opens out into the opening for discharging the moistened calibrating gas and which comprises a bore to the water surface, whereby the chamber is preferably delimited by two components. The interior of the chamber expands in a funnel-like manner starting from the opening for discharging the calibrating gas as well as the bore to the water surface.

The arrangement of the moistening apparatus depends on the gas flow quantities that are to be moistened. For a gas flow quantity of approx. 5 ml/min, for example, a round container with an inner volume of approx. 0.5 ml is fully sufficient. The distance of the water discharge from the floor of the moistener is selected in such a way that during the flow-off of the water a sufficient residual quantity of water remains due to the surface tension.

The stabilization of the gas concentration to 0.1 percent of the scheduled value is possible with the method in accordance to the invention within less than ten seconds at a gas flow of 5 ml/min. The stabilization with a common moistening apparatus would require several minutes.

BRIEF DESCRIPTION OF THE DRAWINGS

The invention is now outlined in greater detail by reference to the enclosed drawings, in which.

DETAILED DESCRIPTION OF PREFERRED EMBODIMENTS

Figure 1:
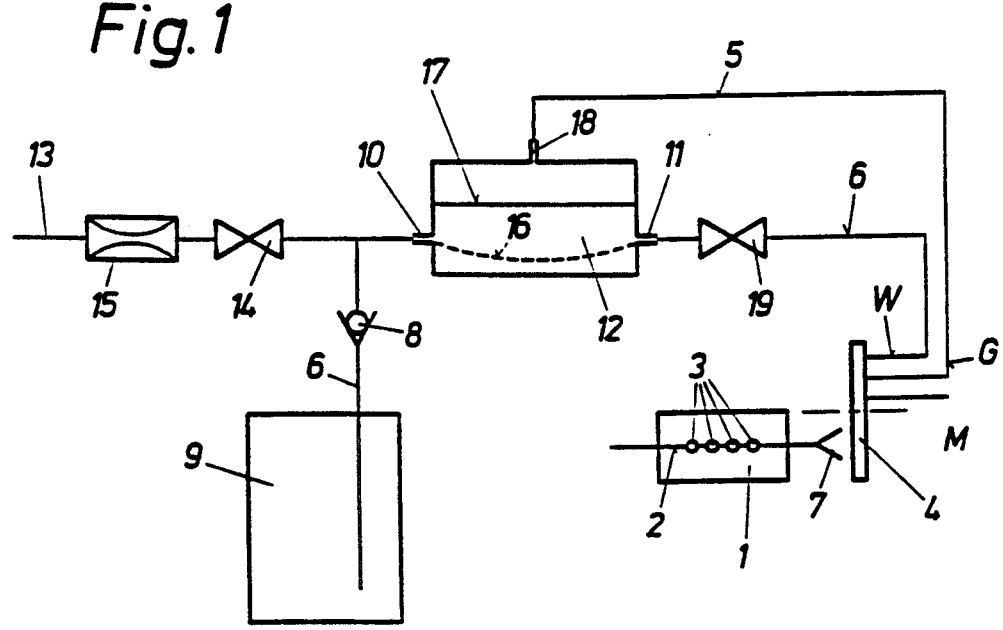
FIG. 1 shows an analyzing device with a moistening device in accordance with the invention.

The analyzing device as represented in FIG. 1 only shows the parts that are essential in connection with the present invention. Thus the analyzing device comprises a measuring module 1 with sensors 3 arranged in a measuring channel 2, which module can be connected to various feed lines through the docking element as known from the above-mentioned EPA 0 297 082. Mentioned are the gas connection G connected with the gas tube 5 for supplying the calibrating gas, the water connection W connected to the washing water tube 6 as well as the connection M for injecting a sample from a capillary tube. The sample can also be inserted directly into the filler socket 7 of the measuring channel 2 which cooperates with the docking element 4. In the washing water tube 6, which is led through a check valve 8 from a water reservoir 9, there is integrated a moistening device 12 through a water inlet 10 and a water outlet 11.

The introduction of the calibrating gas(es) or calibrating gas mixtures to be moistened takes place through tube 13, which gases or gas mixtures come from gas sources not shown here. The introduction preferably takes place via a diaphragm 15 disposed in front of valve 14 and used for stabilizing the gas flow, whereby the dead volume between valve 14 and the diaphragm 15 should be kept low, so as to avoid strong pressure impulses on the moistening device 12.

In an embodiment not shown herein there is the option to dispose diaphragm 15 behind valve 14. However, it is then necessary to take precautions which ensure that no water can reach diaphragm 15. This could, for example, be achieved by providing a gas-permeable, but water-impermeable membrane.

The introduction of the calibrating gas into the moistening device 12 takes place in the shown example through the water inlet 10, whereby the calibrating gas moves over the water surface 16, is moistened and leaves the moistening device 12 after passing a gas-permeable and water vapour-permeable blocking device 17 through an opening 18 which is arranged above the blocking device 17 and connected with gas tube 5.

For the supply of moistened calibrating gases and for the washing process the analyzing device only requires two controllable valves, i.e., valve 14 and a valve 19 arranged between the moistening device 12 and the water connection W in the washing water conduit 6. During the washing process valve 14 is closed and valve 19 is open. When the measuring module is supplied with calibrating gas the switching of the valves is vice-versa.

Figure 2:
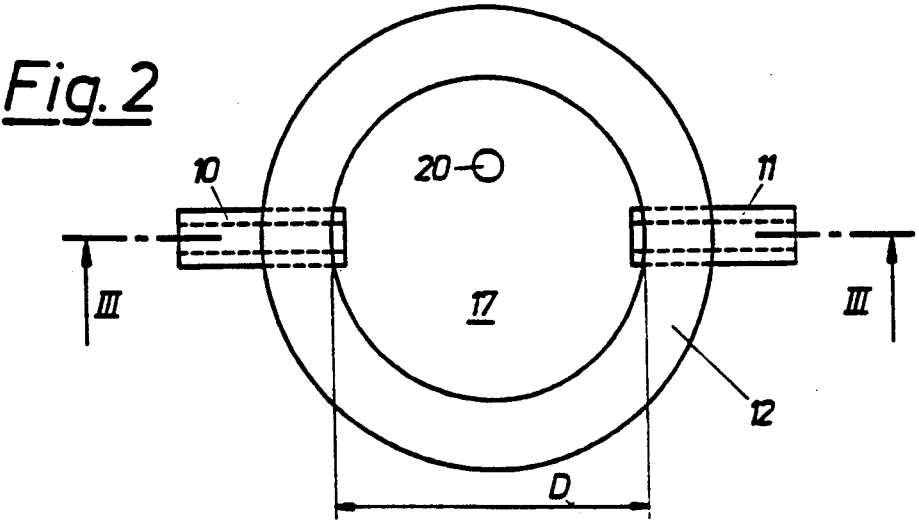
FIG. 2 shows the moistening device in detail.
Figure 3:
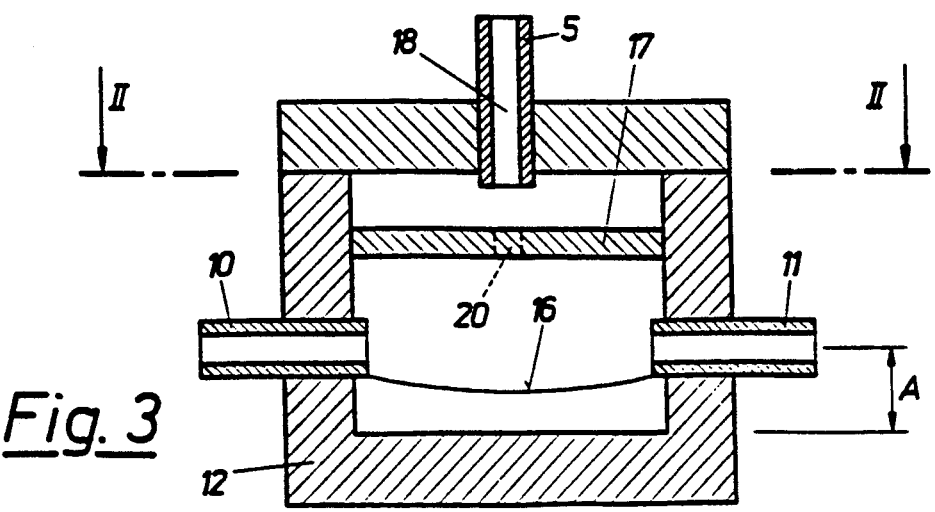
FIG. 3 shows a section along the line III—III in FIG. 2.

FIGS. 2 and 3 show possible embodiments of a moistening device in accordance with FIG. 1. The same components are provided with the same reference numbers. Due to the small dimensions of the moistening device 12 with a diameter D in the vicinity of 10 mm, which device is provided, for example, in the form of a cylindrical container, a water level with the height A of a few millimeters comes about depending on the height of the water outlet 11, whereby the water surface is concavely bent due to the surface tension of the water. The moisture device 12 thus only contains a few 100 μl of water. As shown, the blocking device 17 may be arranged as small disk-shaped plates with a small eccentric bore 20, which prevents the entrainment of water droplets into the gas conduit 5.

Figure 4:
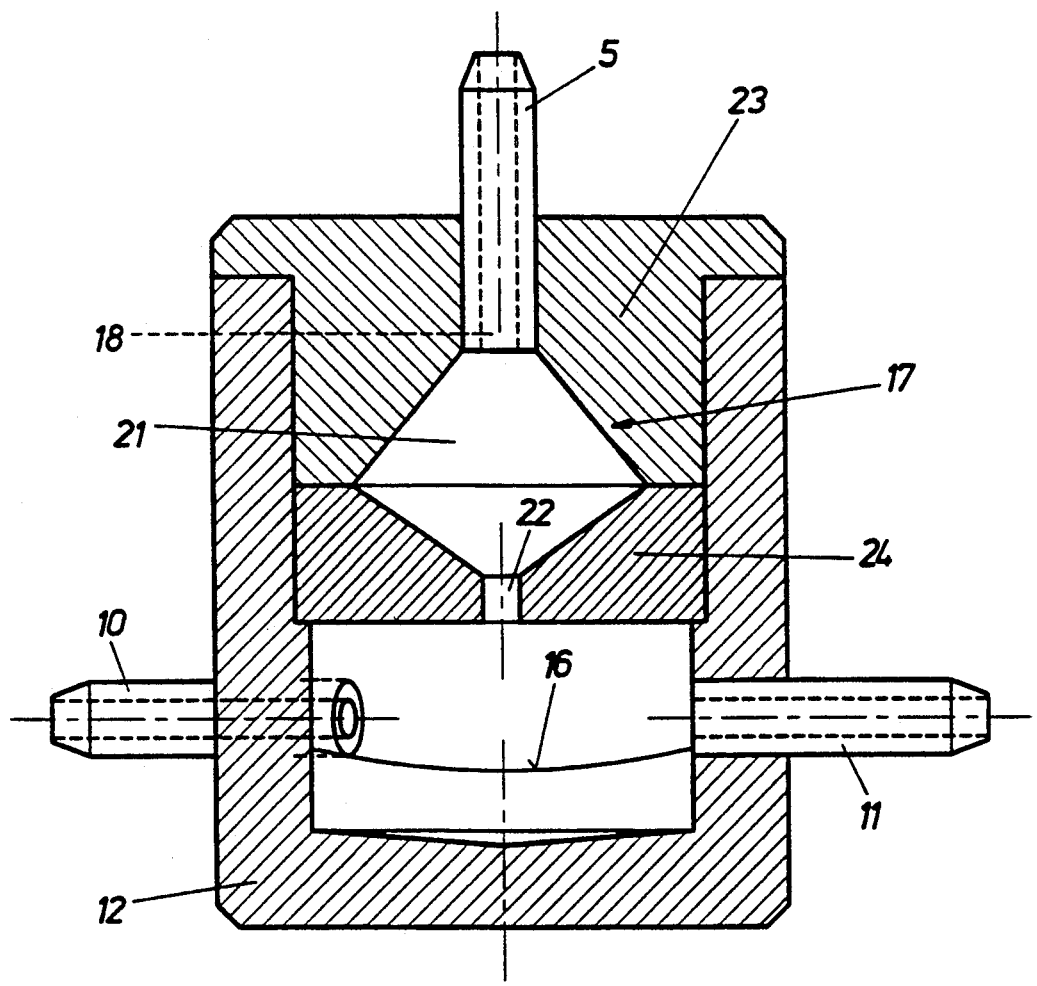
FIG. 4 shows an embodiment in accordance with FIG. 3.

In the embodiment of FIG. 4 the blocking device 17 comprises a chamber 21 for separating water drops. The chamber 17 is delimited by two components 23 and 24, whereby the gas conduit 5 is glued into component 23 and component 24 comprises a bore 22 to the water surface 16. The interior of chamber 21 expands in a funnel-like manner starting from opening 18 and bore 22, which allows any existing drops to flow off easily.

Within the scope of the invention it is also possible that the gas to be moistened can be introduced through several openings disposed around the circumference of the moistening chamber or that the water inlet is disposed in the floor of the moistening device.

I claim:

1. Analyzing device for examining body fluids which comprises a measuring module having a measuring channel, a moistening device, and at least one conduit connected between said moistening device and said measuring module to supply water and moistened calibrating gas to the measuring channel, said moistening device comprising housing means defining a first chamber for water; water outlet means connected to said housing for removing water from said first chamber and for defining a level of water in said first chamber; fluid inlet means connected to said housing at said level of water for supplying calibrating gas into said chamber; and gas outlet means for removing moistened calibrating gas from said first chamber; said calibrating gas passing from said fluid inlet means over a surface of said water to become moistened prior to passing through said gas outlet means.

2. Analyzing device as claimed in claim 1, including means to deliver water and calibrating gas to said fluid inlet means.

3. Analyzing device as claimed in claim 1, including a gas- and water vapor-permeable blocking means located in said housing to define a second chamber above said first chamber, said gas outlet means being connected to said housing to communicate with said second chamber.

4. Analyzing device as claimed in claim 3, wherein said blocking means is a gas- and water vapor-permeable membrane.

5. Analyzing device as claimed in claim 3, wherein said blocking means includes a bore through which gas and water vapor can pass from said first chamber into said second chamber and through which water drops can return to said first chamber.

6. Analyzing device as claimed in claim 5, wherein said second chamber, as it extends from said bore to said gas outlet means, has a cross-section which first expands as a first funnel and then contracts as an inverted, second funnel.

* * * * *